United States Patent
Hong et al.

(10) Patent No.: US 9,615,399 B2
(45) Date of Patent: Apr. 4, 2017

(54) IMPLANTED HUMAN BODY SENSOR NETWORK

(75) Inventors: Choong Seon Hong, Yongin-si (KR); Rossi Kamal Md, Yongin-si (KR); Obaidur Rahman, Yongin-si (KR)

(73) Assignee: UNIVERSITY-INDUSTRY COOPERATION GROUP OF KYUNG-HEE UNIVERSITY, Yongin-si, Gyeonggi-Do (KR)

(*) Notice: Subject to any disclaimer, the term of this patent is extended or adjusted under 35 U.S.C. 154(b) by 226 days.

(21) Appl. No.: 14/241,999

(22) PCT Filed: Apr. 18, 2012

(86) PCT No.: PCT/KR2012/003962
§ 371 (c)(1),
(2), (4) Date: Feb. 28, 2014

(87) PCT Pub. No.: WO2013/032109
PCT Pub. Date: Mar. 7, 2013

(65) Prior Publication Data
US 2014/0285359 A1   Sep. 25, 2014

(30) Foreign Application Priority Data
Sep. 1, 2011   (KR) .................. 10-2011-0088662

(51) Int. Cl.
*H04W 84/18*   (2009.01)
*H04B 13/00*   (2006.01)
(Continued)

(52) U.S. Cl.
CPC .......... *H04W 84/18* (2013.01); *A61B 5/0031* (2013.01); *A61B 5/02055* (2013.01);
(Continued)

(58) Field of Classification Search
CPC .......... A61B 2560/0266; A61B 5/0031; A61B 5/02055; H04B 13/005; H04W 24/00;
(Continued)

(56) References Cited

U.S. PATENT DOCUMENTS

2006/0126501 A1* 6/2006 Ramaswamy ...... G06F 11/2097
370/221
2010/0269501 A1* 10/2010 Parrella .................... F24J 3/082
60/641.2

(Continued)

FOREIGN PATENT DOCUMENTS

KR   1020090015487 A   2/2009

OTHER PUBLICATIONS

International Search Report mailed Nov. 28, 2012 for PCT/KR2012/003962.

*Primary Examiner* — James Yang
*Assistant Examiner* — Laura Nguyen
(74) *Attorney, Agent, or Firm* — Hauptman Ham, LLP

(57) ABSTRACT

The present invention relates to a sensor network, and more particularly, to an implanted sensor network in a human body sensor network in which a plurality of sensor nodes are implanted in the human body to detect biosignals of the human body, wherein the implanted sensor network can prevent the temperature of a sensor node implanted in a human body from rising and thus protect the human body from injury caused thereby.

5 Claims, 6 Drawing Sheets

(51) Int. Cl.
*A61B 5/00* (2006.01)
*A61B 5/0205* (2006.01)
*A61B 5/02* (2006.01)
*A61B 5/145* (2006.01)

(52) U.S. Cl.
CPC .............. *H04B 13/005* (2013.01); *A61B 5/02* (2013.01); *A61B 5/14532* (2013.01); *A61B 5/14542* (2013.01); *A61B 2560/0266* (2013.01)

(58) Field of Classification Search
CPC ..... H04W 24/02; H04W 24/04; H04W 84/18; H04W 84/20; G05B 2219/23043
See application file for complete search history.

(56) References Cited

U.S. PATENT DOCUMENTS

| | | | |
|---|---|---|---|
| 2012/0051314 A1* | 3/2012 | Goyal | H04L 9/0833 370/329 |
| 2013/0182558 A1* | 7/2013 | Orten | H04W 84/18 370/216 |

* cited by examiner

FIG. 8

| ID | Address | Cluster | Role |
|---|---|---|---|
| 0000 | 248,595,1 | 1 | B |
| 0001 | 248,595,2 | 1 | P |
| 0010 | 248,595,3 | 1 | S |
| 0011 | 248,595,4 | 1 | S |
| 0100 | 248,596,1 | 2 | B |
| 0101 | 248,596,2 | 2 | P |
| 0110 | 248,596,3 | 2 | S |
| 0111 | 248,597,1 | 3 | B |
| 1000 | 248,597,2 | 3 | P |
| 1001 | 248,597,3 | 3 | S |

IMPLANTED HUMAN BODY SENSOR NETWORK

TECHNICAL FIELD

The present invention relates to a sensor network, and more particularly, to an implantable sensor network, in which in a human body sensor network implanting a plurality of sensor nodes in a human body and sensing biomedical signals of the human body, damage inflicted on the human body by increase of temperature of the sensor nodes implanted in the human body can be prevented.

BACKGROUND ART

A human body sensor network is a network in which sensor nodes are installed in a human body in a wearable form of putting the sensor nodes on a user or attaching the sensor nodes to the human body or in an implanted form of implanting the sensor nodes in the human body to monitor biomedical signals such as blood clucose contents, blood pressure, oxygen saturation, temperature, electrocardiogram and the like of the user and wirelessly transmit the monitored biomedical signals to a predetermined terminal, and the human body sensor network can be widely applied to a service such as U-health or the like by transmitting the information collected by the sensor nodes to an appropriate place such as a hospital or the like in real-time through a cellular phone or a small-scale base station.

When the sensor node implanted in the human body (hereinafter, referred to as "implant sensor node") in the human body sensor network monitors biomedical signals or transmits the monitored biomedical signals to the cellular phone or the small-scale base station, it generates heat. The heat generated by the implant sensor node bring a great danger to a person in the long run since it may kill body cells.

Various algorithms have been proposed to control the heat generated by the implant sensor node in the implantable body sensor network to be lower than a predetermined threshold temperature.

An algorithm proposed first as a routing algorithm considering the heat generated by the implant sensor node in the implantable body sensor network is a Thermal-Aware Routing Algorithm (TARA) algorithm. If temperature of the implant sensor node increases to be higher than the threshold temperature, the TARA algorithm controls increase of temperature of the implant sensor node by allowing the implant sensor node, the temperature of which is increased to be higher than the threshold temperature, to stop relaying transmission and reception of data monitored by neighboring sensor nodes.

Meanwhile, a Least Temperature Routing (LTR) algorithm has been proposed as another routing algorithm considering the heat generated by the implant sensor node in a conventional implantable body sensor network. When the biomedical signals monitored by the implant sensor node is transmitted to a destination node, the Least Temperature Routing algorithm selects a neighboring implant sensor node having lowest temperature among implant sensor nodes in the neighborhood of the implant sensor node and transmits the monitored data to the destination node.

DISCLOSURE OF INVENTION

Technical Problem

However, the conventional techniques described above relate to an algorithm for determining a routing path to control temperature of implant sensor nodes configuring a transmission routing path to be lower than a threshold temperature when biomedical signals monitored by the implant sensor nodes are transmitted to a destination node in an implantable body sensor network, and a method of continuously maintaining a role of an implant sensor node without doing any harm to a user when temperature of the implant sensor node increases to be higher than a threshold temperature by the operation of the implant sensor node for monitoring the biomedical signals or transmitting and receiving data in the implantable body sensor network is not researched or developed at all.

Actually, the implantable body sensor network is a network for monitoring biomedical signals of a patient by implanting sensor nodes in the body of the patient, and it is important in relation to the life of the patient to ceaselessly monitor the biomedical signals of the patient in real-time. Accordingly, if the operation of the implant sensor node cannot be stopped even when temperature of the implant sensor node increases to be higher than the threshold temperature and, furthermore, if the implant sensor node continuously operates at a temperature higher than the threshold temperature, a danger may occur in the body of the patient.

However, the conventional implantable body sensor network is only interested in a method of routing a biomedical signal sensed by the implant sensor node and has a problem in that it does not propose at all a method of continuously maintaining the operation of the implant sensor node when temperature of the implant sensor node itself increases.

The present invention has been made to solve the problem of the conventional implantable body sensor network described above, and it is an object of the present invention to provide an implantable body sensor network, in which implant sensor nodes configuring the implantable body sensor network are controlled to continue to operate even when temperature of the implant sensor nodes increases to be higher than a threshold temperature which may do harm to a human body.

Another object of the present invention is to provide an implantable body sensor network, in which implant sensor nodes configuring the implantable body sensor network are divided into a plurality of clusters, and implant sensor nodes configuring each cluster are classified as an active node, a relay node and a substitute node so that when an event such as increase of temperature of the active node to be higher than a threshold temperature is generated in each cluster, a control device directly controls operation of the active node or the substitute node although the relay node fails to control operation of the substitute node.

Technical Solution

To achieve the above objects, in one aspect, the present invention provides an implantable body sensor network including: a plurality of implant sensor nodes implanted in a human body; and a control device for creating a cluster by transmitting cluster information to the plurality of implant sensor nodes, and setting roles of the implant sensor nodes configuring the created cluster to any one of a relay node, a substitute node and an active node. Here, the substitute node transmits a detailed event item of the substitute node received from the control device to the relay node to join and store the detailed event item of the substitute node in the relay node and, if an event of the detailed event item is generated by the active node, performs a role of the active node through relay of the relay node.

The control device includes: a cluster creation unit for creating a cluster of implant sensor nodes having a same cluster identifier by transmitting a cluster identifier to the plurality of implant sensor nodes; a node setting unit for setting the implant sensor nodes configuring the created cluster to any one of a relay node, a substitute node and an active node; an operation control unit for stopping the operation of the active node and starting the operation of the substitute node when the operation control unit receives an event confirmation message from the active node; and a database unit for storing the cluster identifier, identifiers of the relay node, the substitute node and the active node configuring the cluster, and the detailed event item of the substitute node configuring the cluster.

Here, the relay node receives the detailed event item from the set substitute node, and when the joining and storing of the detailed event item of the substitute node is completed, the relay node transmits a join completion message of the detailed event item to the control device.

Meanwhile, the relay node stores the detailed event item and the identifier of the substitute node, and when receiving an event generation message from the active node, the relay node searches for a substitute node of the detailed event item corresponding to the event generation message, transfers the event confirmation message to the searched substitute node and the control device, and receives an event response message from the substitute node in response to the event confirmation message.

Preferably, the active node transmitting the event generation message stops its operation. The substitute node receiving the event confirmation message starts its operation, creates an operation message and transmits the operation message to the relay node, and the relay node transmits the received operation message to the control device.

If the control device does not the operation confirmation message from the relay node after receiving the event generation message from the active node of the cluster, the control device controls the stop and start of the operation of the active node and the substitute node of the cluster whose the operation confirmation message is not received.

The control device determines whether or not the join completion message is received from the relay node of the cluster, and if an event generation message is received from the active node of the cluster whose the join completion message is not received, the control device directly controls the stop and start of the operation of the active node and the substitute node configuring the cluster whose the join completion message is not received.

Advantageous Effects

The implantable body sensor network in accordance with the present invention has the following various effects compared with a conventional implantable body sensor network.

First, the implantable body sensor network according to the present invention divides implant sensor nodes configuring the implantable body sensor network into a plurality of clusters, classifies implant sensor nodes configuring each cluster as an active node, a relay node and a substitute node, and stops operation of the active node and operates the substitute node when temperature of the active node increases to be higher than a threshold temperature which may do harm to a human body, and thus operation of the active node may be continued through the substitute node.

Second, since the implantable body sensor network according to the present invention directly controls operation of the substitute node or the active node through a control device even when an event such as increase of temperature of the active node to be higher than a threshold temperature is generated in a cluster and the relay node fails to control the substitute node to operate instead of the active node, biomedical signals of a patient may be safely monitored without stopping the operation of the active node in the implantable body sensor network related to the life of the patient.

BRIEF DESCRIPTION OF THE DRAWINGS

The above and other objects, features and advantages of the present invention will be apparent from the following detailed description of the preferred embodiments of the invention in conjunction with the accompanying drawings, in which:

FIG. 8 is a view showing an example of a database unit according to an embodiment of the present invention.

BEST MODE FOR CARRYING OUT THE INVENTION

Figure 1:
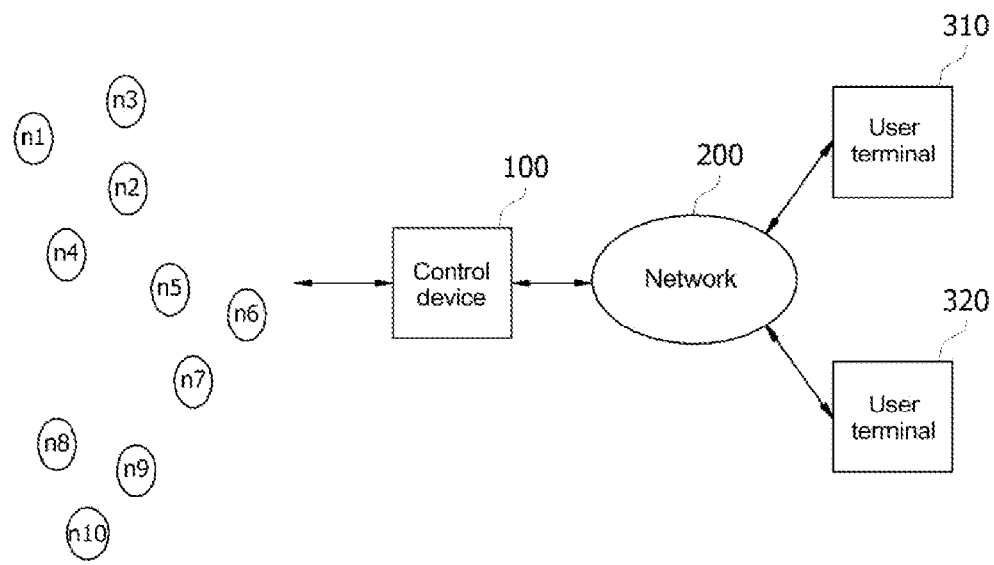
FIG. 1 is a functional block diagram showing an implantable body sensor network according to an embodiment of the present invention.

FIG. 1 is a functional block diagram showing an implantable body sensor network according to an embodiment of the present invention.

A plurality of implant sensor nodes n1 to n10 is implanted in a human body, and the plurality of implant sensor nodes configures a cluster under the control of a control device 100.

The control device 100 provides information on the cluster to the plurality of implant sensor nodes, and the implant sensor nodes are divided into different clusters based on the cluster information, and roles of the implant sensor nodes in each cluster are set to any one of an active node, a relay node and a substitute node. Here, the active node is an implant sensor node implanted in a human body and monitors biomedical signals such as blood clucose contents, blood pressure, oxygen saturation, temperature, electrocardiogram and the like of a user, and the substitute node is an implant sensor node performing the role of the active node instead of the active node when an event set by the active node is generated, and the relay node is an implant sensor node which searches for a substitute node for performing an operation corresponding to an event generated by the active node based on a detailed event item of the substitute node and relays the event by informing the searched substitute node of generation of the event so that the substitute node may continue the operation of monitoring the biomedical signals instead of the active node.

The control device 100 is connected to a user terminal 310 or 320 through a wired/wireless network 200, and biomedical signals of the user transmitted from each cluster to the control device 100 are transmitted from the control device 100 to the user terminal 310 or 320 through the network 200 in response to a request of the user terminal 310 or 320.

Figure 2:
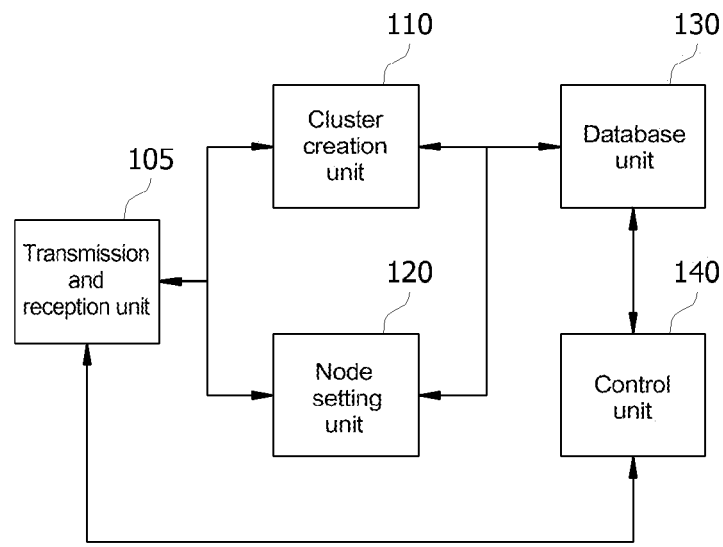
FIG. 2 is a functional block diagram showing a control device according to an embodiment of the present invention.
Figure 3:
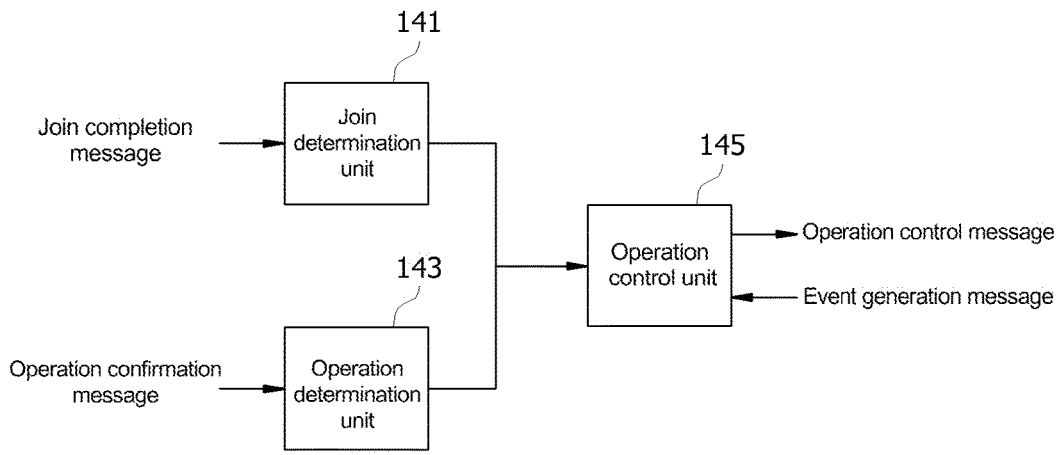
FIG. 3 is a view showing an example of a cluster formed by a control device of the present invention.

FIG. 2 is a functional block diagram showing a control device according to an embodiment of the present invention, FIG. 3 is a view showing an example of a cluster formed by a control unit of the present invention, and FIG. 8 is a view showing an example of a database according to an embodiment of the present invention.

Describing with reference to FIG. 2, a cluster creation unit 110 creates a plurality of clusters from implant sensor nodes based on identifiers of the implant sensor nodes stored in a database unit 130. For example, a first cluster is created by setting implant sensor nodes having descriptors such as 0000, 0001, 0010 and 0011 as cluster identifier 1. In the same manner, a second cluster is created by setting implant sensor nodes having descriptors such as 0100, 0101 and 0110 as cluster identifier 2.

The cluster creation unit 110 configures one cluster using at least three or more implant sensor nodes. The cluster creation unit 110 stores the identifier of the cluster to which the implant sensor nodes belong into the database unit 130.

A node setting unit 120 sets the role of implant sensor nodes having the same cluster identifier to any one of an active node, a relay node and a substitute node based on the cluster identifier created by the cluster creation unit 110. The node setting unit 120 sets only one relay node and at least one or more active nodes and substitute nodes among the implant sensor nodes configured in each cluster.

Meanwhile, if an event is generated by an active node of each cluster, the node setting unit 120 specifies a detailed event item of a substitute node. Here, the event is a situation of stopping the operation of the active node and starting the operation of the substitute node instead of the active node, and the detailed event item is a role of the substitute node in the case where an event is generated by the active node. An example of the event is increase of temperature to be higher than a threshold temperature, and an example of the detailed event item is performing an operation instead of the active node when an event of increasing temperature of the active node to be higher than the threshold temperature is generated.

The cluster identifier created by the cluster creation unit 110 is transmitted to all the implant sensor nodes implanted in a user through a transmission and reception unit 105, and information on the role of an implant sensor node set by the node setting unit 120 is transmitted to the implant sensor node through the transmission and reception unit 105, and the detailed event item of a substitute node is transmitted to the substitute node through the transmission and reception unit 105. The cluster identifier, the role of an implant sensor node and the detailed event item will be hereinafter referred to as cluster information, and all of the cluster information is combined by the cluster creation unit 110 and transmitted to the implant sensor node or combined by the node setting unit 120 and transmitted to the implant sensor node in order to prevent waste of energy according to transmission and reception of data. In addition, in another embodiment, the cluster identifier is transmitted from the cluster creation unit 110 to the implant sensor node, and the role information and the detailed event item are transmitted from the node setting unit 120 to the implanted sensor unit.

The control unit 140 creates an operation control message for controlling stop or start of operation of the active node or the substitute node and transmits the created operation control message to the active node or the substitute node through the transmission and reception unit according to whether or not a join completion message informing completion of join of a detailed event item is received from the relay node of each cluster through the transmission and reception unit 105 or whether or not an operation confirmation message informing start of the operation of the substitute node is received from the relay node.

Describing in further detail with reference to FIG. 3 showing an example of the functional block diagram of the control unit according to the present invention, a join determination unit 141 determines whether or not a join completion message informing whether or not a detailed event item of a substitute node of each cluster has joined the relay node is received from the relay node included in each cluster. If an event is generated by an active node of a specific cluster, an operation determination unit 143 determines whether or not an operation confirmation message for confirming generation of an event in the substitute node of the specific cluster is received from the relay node of the specific cluster.

If an event is generated by an active node of a specific cluster, an operation control unit 145 receives an event generation message from the active node of the specific cluster, and if a join completion message is not received from the relay node of the specific cluster receiving the event generation message, the operation control unit 145 creates an operation control message for stopping the operation of the active node of the specific cluster and an operation control message for starting operation of a substitute node of the specific cluster and transmits the operation control messages to the active node and the substitute node. Meanwhile, if an event is generated by the active node of the specific cluster, the operation control unit 145 receives an event generation message from the active node of the specific cluster, and if an operation confirmation message is not received from the relay node of the specific cluster receiving the event generation message, the operation control unit 145 creates an operation control message for stopping the operation of the active node of the specific cluster and an operation control message for starting operation of a substitute node of the specific cluster and transmits the operation control messages to the active node and the substitute node.

The operation control unit 145 according to the present invention receives the event generation message directly from the active node generating the event, and if the join completion message or the operation confirmation message is not received from the relay node of the cluster receiving the event generation message, the operation control unit 145 directly controls operation of the active node and the substitute node to prevent continuous operation of the active node while the event is generated or to prevent non-start of the operation of the substitute node while the event is generated by the active node and the operation of the active node is stopped. Accordingly, the implantable body sensor network according to the present invention prevents damage inflicted on a human body by increase of temperature to be higher than a threshold temperature due to continuous operation of the active node in a field directly related to the life of patients, and when the substitute node does not start to operate instead of the active node, it may safely operate a biomedical signal monitoring system by directly controlling start of the operation of the substitute node through the operation control unit.

Figure 4:
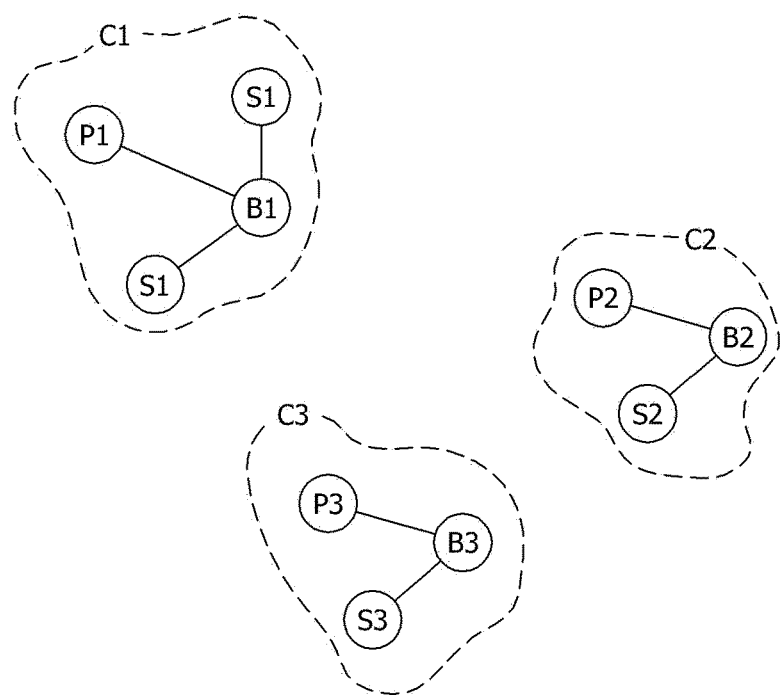
FIG. 4 is a view showing an example of a cluster created by a control device according to the present invention.

Describing an example of the cluster created by the control device according to the present invention in further detail with reference to FIG. 4, the cluster creation unit 110 creates three clusters by assigning a first cluster identifier to implant sensor nodes n1 to n4 among implant sensor nodes n1 to n10 implanted in a user, a second cluster identifier to implant sensor nodes n5 to n7, and a third cluster identifier to implant sensor nodes n8 to n10.

Meanwhile, the node setting unit 120 sets roles of the implant sensor nodes based on the cluster identifiers so that implant sensor nodes configuring the same cluster may respectively operate as any one of an active node, a relay node and a substitute node. For example, implant sensor node n1 among implant sensor nodes configuring a first cluster C1 is set as an active node P1, implant sensor node n2 is set as a relay node B1, and implant sensor nodes n3 and n4 are set as substitute nodes S1 and S1'. Meanwhile, if event 1 is generated by active node P1 for substitute node S1, the node setting unit 120 specifies a detailed event item for starting operation of substitute node S1 instead of active node P1, and if event 2 is generated by active node P1 for substitute node S1', the node setting unit 120 specifies a detailed event item for starting operation of substitute node S1' instead of active node P1.

A cluster to which an implant sensor node implanted in a human body belongs, a role of the implant sensor node in each cluster, and a detailed event item of a substitute node may be set in advance and stored in the database unit 130 as shown in FIG. 8 according to a field to which the present invention applies, and the control device 100 may simply control operation of the active node and the substitute node in a set cluster according to whether or not a join completion message or an operation confirmation message is received.

Figure 5:
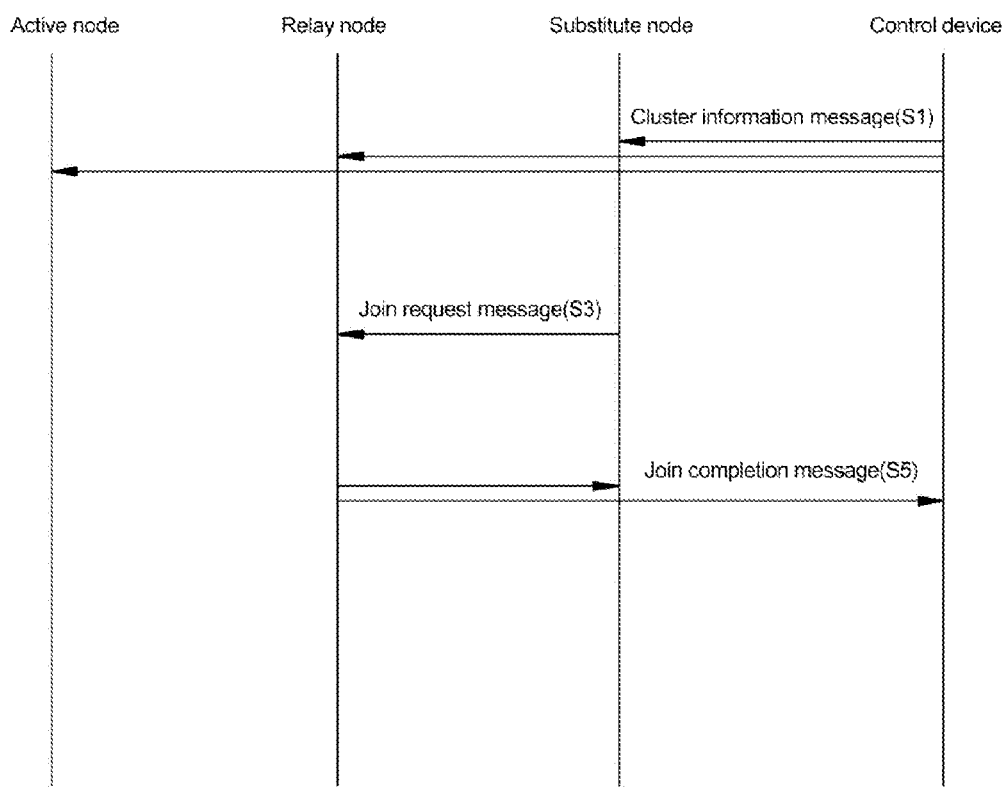
FIG. 5 is a flowchart illustrating a method of creating a cluster in an implantable body sensor network according to the present invention.

FIG. 5 is a flowchart illustrating a method of creating a cluster in an implantable body sensor network according to the present invention.

Describing in further detail with reference to FIG. 5, the control device creates a cluster based on an identifier of an implant sensor node stored in the database unit, sets a role of an implant sensor node and a detailed event item of a substitute node configuring the same cluster identifier in the created cluster, and transmits cluster information including the cluster identifier, the role and the detailed event item to the implant sensor node based on the address of the implant sensor node.

The implant sensor node set as a substitute node in each cluster transmits a join request message for storing and joining the received detailed event item in the relay node S3, and the relay node receiving the join request message transmits a join completion message to the substitute node and the control device.

Figure 6:
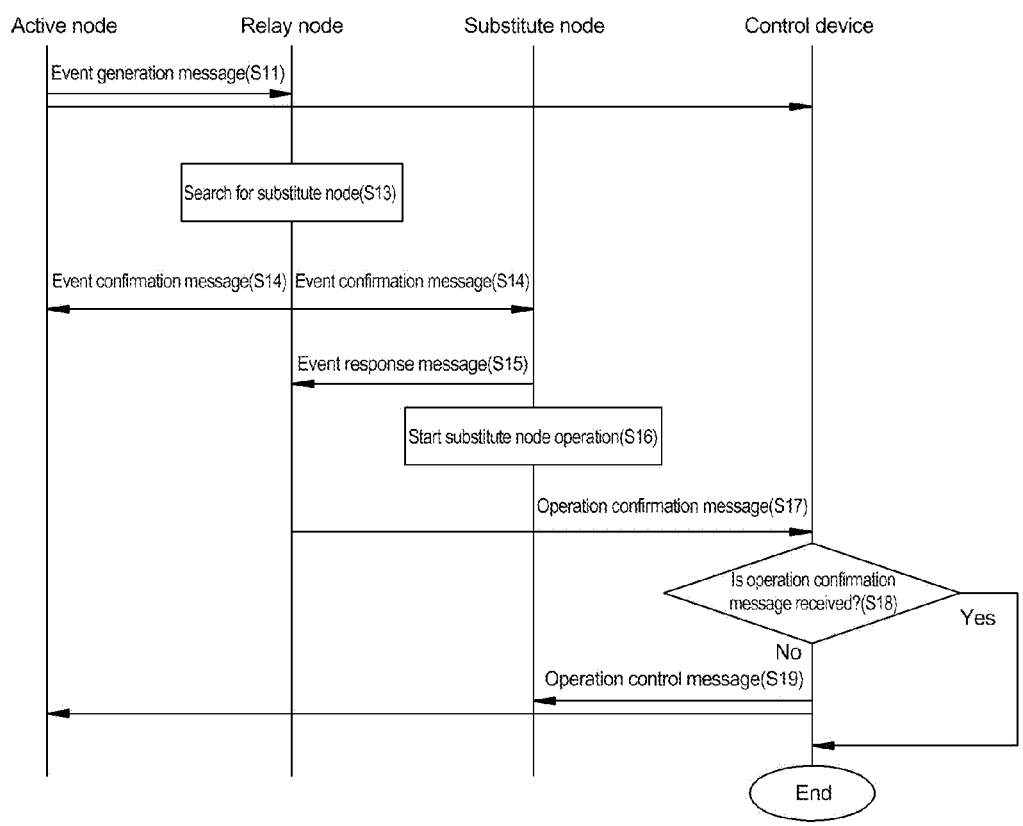
FIG. 6 is a flowchart illustrating a method of controlling the operation of an active node and a substitute node in an implantable body sensor network according to the present invention.

FIG. 6 is a flowchart illustrating a method of controlling the operation of an active node and a substitute node in an implantable body sensor network according to the present invention.

Describing in further detail with reference to FIG. 6, if an event is generated, the active node creates an event generation message and transmits the event generation message to the relay node and the control device. The relay node receiving the event generation message searches for a substitute node of a detailed event item corresponding to the generated event S13 and transmits an event confirmation message to the searched substitute node and the active node S14. The active node receiving the event confirmation message stops operation.

Meanwhile, the substitute node receiving the event confirmation message transmits an event response message to the relay node S15 and starts an operation the same as that of the active node instead of the active node S16. The relay node receiving the event response message from the substitute node creates an operation confirmation message and transmits the operation confirmation message to the control device to inform that operation of the substitute node has been started S17. After receiving the event generation message, the control device determines whether or not the operation confirmation message is received within a predetermined threshold time from the relay node of the cluster generating the event S18, and if the operation confirmation message is not received from the relay node of the cluster generating the event, the control device creates an operation control message for stopping the operation of the active node and an operation control message for starting the operation of the substitute node and transmits the operation control messages to the active node and the substitute node S19.

As described in FIG. 6, although the substitute node does not receive the event confirmation message and thus does not start to operate or the active node does not receive the event confirmation message and continues to operate in the implantable body sensor network according to the present invention, the control device may safely operate the implantable body sensor network by directly controlling the operation of the active node and the substitute node.

Figure 7:
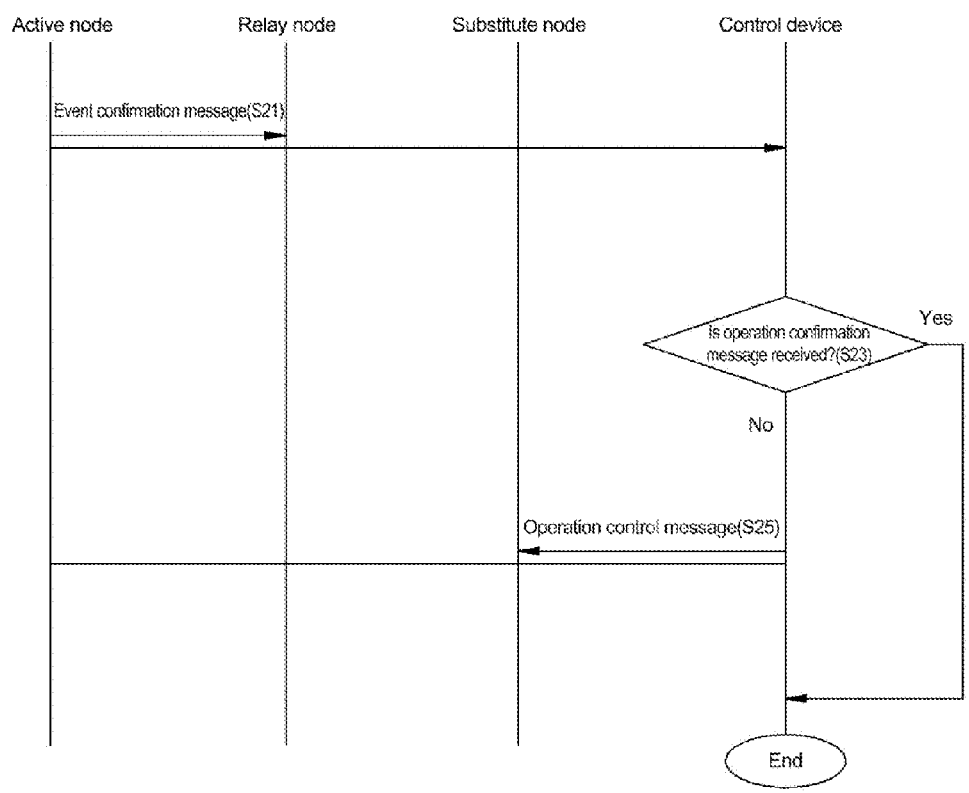
FIG. 7 is a flowchart illustrating a method of controlling the operation of an active node and a substitute node in an implantable body sensor network according to the present invention.

FIG. 7 is a flowchart illustrating a method of controlling the operation of an active node and a substitute node in an implantable body sensor network according to the present invention.

Describing in further detail with reference to FIG. 7, if an event is generated, the active node creates an event generation message and transmits the event generation message to the relay node and the control device S21. When the event generation message is received, the control device determines whether or not a join completion message is received from the relay node of the cluster generating the event S23, and if the join completion message is not received from the relay node of the cluster generating the event, the control device creates an operation control message for stopping the operation of the active node and an operation control message for starting the operation of the substitute node and transmits the operation control messages to the active node and the substitute node S25.

As described in FIG. 7, although the substitute node fails to join and store a detailed event item in the relay node and thus the active node continuously maintains operation and the substitute node does not start operation even when an event is generated by the implantable body sensor network according to the present invention, the control device may safely operate the implantable body sensor network by directly controlling the operation of the active node and the substitute node.

While the present invention has been described in connection with the exemplary embodiments illustrated in the drawings, they are merely illustrative embodiments, and the invention is not limited to these embodiments. It is to be understood that various equivalent modifications and variations of the embodiments can be made by a person having an ordinary skill in the art without departing from the spirit and scope of the present invention. Therefore, the true technical scope of the present invention should be defined by the technical spirit of the appended claims.

The invention claimed is:

1. An implantable body sensor network, comprising:
a plurality of implant sensor nodes implanted in a human body; and
a control device configured to
create a cluster by transmitting cluster information to the plurality of implant sensor nodes, and
set a role of each of the implant sensor nodes of the created cluster to be one of a relay node, a substitute node and an active node,
wherein the substitute node is configured to transmit a detailed event item of the substitute node received from the control device to the relay node to join and store the detailed event item of the substitute node in the relay node, and
wherein the substitute node is further configured to, when an event of the detailed event item is generated by the active node, perform a role of the active node through a relay of the relay node,
wherein the control device is further configured to, when the control device does not receive an operation confirmation message from the relay node of the cluster after receiving an event generation message from the active node of the cluster, directly control a stop and a start of an operation of the active node of the cluster which includes the relay node that does not transmit the operation confirmation message and an operation of the substitute node of the cluster which includes the relay node that does not transmit the operation confirmation message,
wherein the control device is further configured to determine whether or not a join completion message is received from the relay node of the cluster, and
wherein the control device is further configured to, when the event generation message is received from the active node of the cluster which includes the relay node that does not transmit the join completion message, directly control the stop and the start of the operation of the active node of the cluster which includes the relay node that does not transmit the join completion message, and the operation of the substitute node of the cluster which includes the relay node that does not transmit the join completion message.

2. The network according to claim 1, wherein the control device is further configured to
create the cluster by clustering implant sensor nodes having the same cluster identifier by transmitting a cluster identifier to the plurality of implant sensor nodes;
set the role of the each of the implant sensor nodes of the created cluster to be one of the relay node, the substitute node and the active node;
stop the operation of the active node and starting the operation of the substitute node when the control device receives the operation confirmation message from the relay node, and
store the cluster identifier, identifiers of the relay node, the substitute node and the active node of the cluster, and the detailed event item of the substitute node of the cluster.

3. The network according to claim 2, wherein the relay node is configured to
receive the detailed event item from a set substitute node, and
join and store the detailed event item and the identifier of the substitute node, and
wherein the relay node is further configured to, when the joining and storing of the detailed event item of the substitute node is completed, transmit the join completion message of the detailed event item to the control device.

4. The network according to claim 2, wherein the active node is configured to,
when the event of the detailed event item is generated, transmit the event generation message to the relay node and the control device, and
wherein the relay node is further configured to, when receiving the event generation message from the active node,
search for a substitute node of the detailed event item, corresponding to the event generation message,
transmit an event confirmation message to the searched substitute node, and
receive an event response message from the substitute node in response to the event confirmation message.

5. The network according to claim 4, wherein the active node transmitting the event generation message is configured to stop its operation,
wherein the substitute node receiving the event confirmation message is configured to start its operation, and
wherein the relay node receiving the event response message is configured to transmit the operation confirmation message to the control device.

* * * * *

UNITED STATES PATENT AND TRADEMARK OFFICE
CERTIFICATE OF CORRECTION

PATENT NO. : 9,615,399 B2  
APPLICATION NO. : 14/241999  
DATED : April 4, 2017  
INVENTOR(S) : Choong Seon Hong et al.

Page 1 of 1

It is certified that error appears in the above-identified patent and that said Letters Patent is hereby corrected as shown below:

On the Title Page

Item (22):
The Date of PCT Filed "Apr. 18, 2012" should read "May 18, 2012".

Signed and Sealed this
Thirtieth Day of May, 2017

Michelle K. Lee
*Director of the United States Patent and Trademark Office*